United States Patent [19]

Yamanaka et al.

[11] 4,365,066
[45] Dec. 21, 1982

[54] 2(4-N-HEXADECYL AMINO OR OXY PHENYL) 5 ETHOXY OXAZOLEACETIC ACID DERIVATIVES

[75] Inventors: Tsutomu Yamanaka, Nakatsu; Mitsuharu Sano, Shinyoshitomimura; Hiroshi Yasuda, Nakatsu, all of Japan

[73] Assignee: Yoshitomi Pharmaceutical Industries Ltd., Japan

[21] Appl. No.: 253,932
[22] PCT Filed: Nov. 25, 1980
[86] PCT No.: PCT/JP80/00287
§ 371 Date: Jul. 28, 1981
§ 102(e) Date: Apr. 14, 1981
[87] PCT Pub. No.: WO81/01553
PCT Pub. Date: Jun. 11, 1981

[30] Foreign Application Priority Data

Nov. 28, 1979 [JP] Japan .................. 54/154714

[51] Int. Cl.$^3$ ............... C07D 263/42; A61K 31/42
[52] U.S. Cl. ................................ 548/228; 424/272
[58] Field of Search ........................ 548/228

[56] References Cited
U.S. PATENT DOCUMENTS 4,012,412 3/1977 Yamanaka et al. .......... 548/228
4,053,478 10/1977 Yamanaka et al. .......... 548/228
4,175,130 11/1979 Yamanaka et al. .......... 548/228

OTHER PUBLICATIONS

88:89653c, Yamanaka et al., Chemical Abstracts.
86:89792f, Yamanaka et al., Chemical Abstracts.

Primary Examiner—Donald G. Daus
Assistant Examiner—Sharon A. Gibson
Attorney, Agent, or Firm—Larson and Taylor

[57] ABSTRACT

Oxazoleacetic acid derivatives of the formula

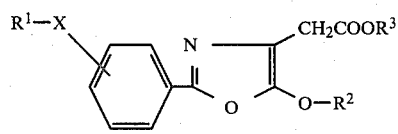

and salts thereof wherein $R^1$ is a higher alkyl group having 10 to 20 carbon atoms, a higher alkenyl group, a benzyl group or a halogen substituted benzyl group; X is O, S or NH; $R^2$ is a lower alkyl group, a phenyl group or a halogen-substituted phenyl group and $R^3$ is a hydrogen atom or a lower alkyl group, having a hypolipidemic activity.

3 Claims, No Drawings

2(4-N-HEXADECYL AMINO OR OXY PHENYL) 5 ETHOXY OXAZOLEACETIC ACID DERIVATIVES

TECHNICAL FIELD AND DISCLOSURE OF THE INVENTION

This invention relates to novel and therapeutically valuable oxazoleacetic acid derivatives of the formula

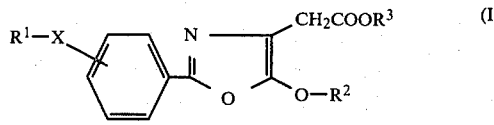

and salts thereof, wherein: R is a higher alkyl group having 10 to 20 carbon atoms (e.g. decyl, dodecyl, tetradecyl, hexadecyl or octadecyl), a higher alkenyl group (e.g. decenyl, dodecenyl, tetradecenyl, hexadecenyl or octadecenyl), a benzyl group or a halogen(fluorine, chlorine, bromine or iodine)-substituted benzyl group; X is O, S or NH; $R^2$ is a lower alkyl group (e.g. methyl, ethyl, propyl or butyl), a phenyl group or a halogen-substituted phenyl group; and $R^3$ is a hydrogen atom or a lower alkyl group.

Examples of the salts of compounds of the formula (I) are inorganic salts, e.g. sodium salts, magnesium salts, calcium salts, aluminum salts, ammonium salts; amine salts, e.g. dimethyl amine salts; trimethyl amine salts; or amino acid salts, e.g. arginine salts, lysine salts.

The compounds of the formula (I) can be prepared according to one of the following methods (1) to (3):

METHOD (1)

In the case of compounds of formula (I) wherein $R^3$ is a lower alkyl group, by dehydrating for ring-closure a compound of the formula

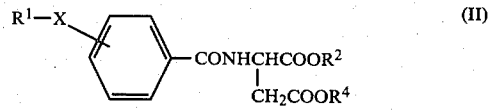

wherein $R^1$, X and $R^2$ are as defined above and $R^4$ is a lower alkyl group.

The reaction is carried out by treating the compound of formula (II) with a dehydrating agent such as phosphorus pentoxide, phosphorus pentachloride, phosphorus oxychloride, thionyl chloride, tosyl chloride or concentrated sulfuric acid, at room temperature or under heating, optionally in a solvent such as benzene, toluene, chloroform or 1,2-dichloroethane. In the case of compounds of formula (II) wherein X is NH, the compound is preferably protected with an amino-protecting group (e.g. formyl, trifluoroacetyl, tosyl, benzyloxycarbonyl or phthalyl), and then subjected to dehydration for ring closure and to removal of the protecting group.

The starting compounds of formula (II) can be prepared in a conventional manner from aspartic acid which may have L-, D- or DL-configuration.

METHOD (2)

In the case of compounds of formula (I) wherein $R^3$ is a hydrogen atom, by hydrolyzing a compound of formula (I) wherein $R^3$ is a lower alkyl group.

The hydrolysis may be carried out with an acid or an alkali, preferably with a diluted alkali solution (e.g. sodium hydroxide or potassium hydroxide) in water, a water-soluble organic solvent (e.g. methanol, ethanol, acetone, dioxan or tetrahydrofuran) or a mixture thereof.

METHOD (3)

In the case of compounds of formula (I) wherein $R^3$ is a lower alkyl group, by reacting a compound of formula (I) wherein $R^3$ is a hydrogen atom (a carboxylic acid) or a functional derivative thereof [e.g. an acid chloride, an acid anhydride, an acid azide, or a reactive ester (e.g. p-nitrophenyl ester or N-hydroxysuccinimide ester)] with a lower alkanol.

The oxazoleacetic acid derivatives and salts thereof of this invention possess an excellent hypolipidemic activity and very low toxicity, as shown by the following experiments, and are useful as drugs for the treatment of atherosclerosis with lipid metabolism disorder or intermediates therefor.

EXPERIMENTS (1) Test Compounds

Compound A: 2-(4-n-Hexadecyloxyphenyl)-5-ethoxy-4-oxazoleacetic acid

Compound B: Sodium 2-(4-n-hexadecylaminophenyl)-5-ethoxy-4-oxazoleacetate

Compound C: 2-(4-n-Hexadecyloxyphenyl)-5-(4-chlorophenoxy)-4-oxazoleacetic acid

Compound D: 2-[4-(4-Chlorobenzyloxy)phenyl]-5-ethoxy-4-oxazoleacetic acid

Compound E: Clofibrate (for comparison)

(2) Test methods and results:

(i) Male Sprague-Dowley rats were used. Each group was composed of 8 animals. Rats were fed a diet containing 1% of cholesterol. The test compound was orally administered to the animal by feeding with the diet to which the compound was blended in a ratio of 0.1% (W/W) for 5 days. Cholesterol and triglyceride in the serum were determined by the standard methods using an autoanalyzer (Technicon Inc.). The levels in the control group were considered as 100% and the reduction rate in the test group was calculated. The results are shown in Table 1.

TABLE 1

| Test Compound | Reduction Rate (%) | |
|---|---|---|
| | Cholesterol | Triglyceride |
| A | 21 | 35 |
| B | 31 | 28 |
| C | 31 | 37 |
| D | 37 | 42 |
| E | 22 | 23 |

(ii) With the exception that rats were fed a conventional diet instead of the diet containing 1% cholesterol, a test was carried out in the same condition (rats used, administration method, period, concentration of test compound and cholesterol and triglyceride determination) as in the above test (i). The reduction rates thus obtained are shown in Table 2.

TABLE 2

| Test Compound | Reduction Rate (%) | |
|---|---|---|
| | Cholesterol | Triglyceride |
| A | 29 | 44 |
| B | 26 | 44 |
| D | 19 | 53 |

TABLE 2-continued

| Test Compound | Reduction Rate (%) | |
| --- | --- | --- |
| | Cholesterol | Triglyceride |
| E | 23 | 34 |

(iii) Male dd-strain mice were used. Each group was composed of 10 animals. The test compound was administered intraperitoneally or orally to the animals. The $LD_{50}$ (mg/kg) was calculated from the mortality within 7 days after administration of the test compound. The results are given in Table 3.

TABLE 3

| | $LD_{50}$ | |
| --- | --- | --- |
| Test Compound | Intraperitoneal administration | Oral administration |
| A | >1,000 mg/kg | >2,500 mg/kg |
| B | >1,000 mg/kg | >2,500 mg/kg |
| E | >1,000 mg/kg | >1,450 mg/kg |

(iv) Rhesus monkeys having hyperlipemia fed with a diet containing 0.25% cholesterol were used. A diet containing 0.7% (W/W) of the test compound A or B was administered for 15 days. An outstanding reduction activity of blood cholesterol was observed in the administered group as compared with the control group.

In view of various standpoints including the above-mentioned experiments, the compounds (I) and salts thereof of the present invention can be administered safely as drugs for the treatment of atherosclerosis with lipid metabolism disorder, in the form of a phamaceutical preparation with a suitable and conventional carrier or adjuvant which is administered orally without harmful side effects to the patients.

The oral daily dose of the compounds of the present invention for human adults usually ranges from 100 to 1,000 mg.

FORMULATION EXAMPLE

Tablets of 200 mg are prepared from the following compositions:

| Compound A | 200.0 mg |
| --- | --- |
| Lactose | 35.5 mg |
| Microcrystalline cellulose | 10.0 mg |
| Starch | 30.0 mg |
| Talc | 3.5 mg |
| Magnesium stearate | 1.0 mg |
| | 280.0 mg |

REFERENCE EXAMPLE

[Preparation of the starting compounds (II)]

Diethyl N-4(n-hexadecyloxy)benzoyl-L-aspartate

To a solution of 16 g of 4-(n-hexadecyloxy)benzoyl chloride and 9.4 g of diethyl L-aspartate in 140 ml of tetrahydrofuran under ice-cooling was added dropwise 5.0 g of triethylamine with stirring. After stirring under ice-cooling for 90 minutes, the insoluble substances were filtered off. To the filtrate were added ice and ethyl acetate. The organic layer was successively washed with diluted hydrochloric acid, diluted sodium bicarbonate solution and water, dried over anhydrous sodium sulfate, and then concentrated under reduced pressure. The residue was recrystallized from hexane to give 20.3 g of the title compound as white crystals, m.p. 68°–69° C.

The following compound can be prepared in a similar manner as above.

Diethyl N-4-(4-chlorobenzyloxy)benzoyl-L-aspartate, m.p. 91.5°–93° C.

EXAMPLE 1

(a) Ethyl 2-(4-n-hexadecyloxyphenyl)-5-ethoxy-4-oxazoleacetate

To a solution of 20.3 g of diethyl N-4-(n-hexadecyloxy)benzoyl-L-aspartate in 150 ml of toluene was added 10 ml of phosphorus oxychloride. The resulting solution was refluxed under heating for 75 minutes. After cooling, the solution was poured into a mixture of ice and potassium carbonate. After stirring for a while, to the resulting solution was added ethyl acetate and the whole solution was shaped to separate an organic layer. The organic layer was washed with water, dried over anhydrous sodium sulfate and concentrated under reduced pressure. The residue was recrystallized from hexane to give 20 g of the title compound, m.p. 44°–45° C.

(b) 2-(4-n-Hexadecyloxyphenyl)-5-ethoxy-4-oxazoleacetic acid

To a solution of 20 g of ethyl 2-(4-hexadecyloxyphenyl)-5-ethoxy-4-oxazoleacetate in 200 ml of methanol was added a solution of 7.6 g of sodium hydroxide in 20 ml of water under stirring at room temperature and stirred for about 3.5 hours. The reaction mixture was concentrated under reduced pressure. The residue was dissolved in water and the solution was acidified with hydrochloric acid to pH 1 under cooling. The precipitate was filtered off, dried and recrystallized from methanol to give 11.7 g of the title compound of white powder, m.p. 89°–91° C.

The following compounds can be prepared in the same manner as in (a).

Ethyl 2-[4-(4-chlorobenzyloxy)phenyl]-5-ethoxy-4-oxazoleacetate, m.p. 96°–97.5° C.

Ethyl 2-(4-n-dodecyloxyphenyl)-5-ethoxy-4-oxazoleacetate, m.p. 48.5°–49.5° C.

Ethyl 2-(4-n-tetradecyloxyphenyl)-5-ethoxy-4-oxazoleacetate, m.p. 41.5°–42.5° C.

Ethyl 2-(4-n-octadecyloxyphenyl)-5-ethoxy-4-oxazoleacetate, m.p. 54° C.

Ethyl 2-(4-n-hexadecylthiophenyl)-5-ethoxy-4-oxazoleacetate

The following compounds can be prepared in the same manner as in (b):

2-[4-(4-Chlorobenzyloxy)phenyl]-5-ethoxy-4-oxazoleacetic acid, m.p. 130°–131° C.

2-(4-n-Dodecyloxyphenyl)-5-ethoxy-4-oxazoleacetic acid, m.p. 86°–87° C.

2-(4-n-Tetradecyloxyphenyl)-5-ethoxy-4-oxazoleacetic acid, m.p. 88.5°–89° C.

2-(4-n-Octadecyloxyphenyl)-5-ethoxy-4-oxazoleacetic acid, m.p. 77°–78° C.

2-(4-n-Hexadecylthiophenyl)-5-ethoxy-4-oxazoleacetic acid

EXAMPLE 2

Sodium 2-(4-n-hexadecylaminophenyl)-5-ethoxy-4-oxazoleacetate

To a suspension of 46.5 g of 4-(n-hexadecylamino)benzoic acid in 300 ml of pyridine was dropwise added trifluoroacetic anhydride with stirring under ice-cooling in the course of 15 minutes. After the mixture was further stirred at room temperature for 90 minutes, the mixture was poured into ice-water and extracted with ethyl acetate. The organic layer was successively washed with diluted hydrochloric acid and water, dried over anhydrous sodium sulfate and concentrated. To the residual oily N-trifluoroacetyl derivative, without purification, were added 100 ml of thionyl chloride and 300 ml of benzene. The whole mixture was refluxed under heating for 110 minutes and completely concentrated. The residue was reacted and treated with 29.2 g of diethyl L-aspartate in the same manner as described in reference example to give 73 g of diethyl N-[4-(N-trifluoroacetyl-N-n-hexadecylamino)benzoyl]-L-aspartate. To a solution of the oil in 500 ml of toluene was added 40 ml of phosphorus oxychloride. After the mixture was refluxed under heating for 120 minutes, the resulting solution was poured into a mixture of ice and potassium carbonate and then extracted with benzene. The benzene layer was further washed with diluted aqueous potassium carbonate solution and aqueous sodium chloride solution, dried over anhydrous sodium sulfate and concentrated under reduced pressure. The residue obtained, without purification, was dissolved in 300 ml of methanol. To the solution was added a solution of 14 g of sodium hydroxide in 80 ml of water at room temperature and the whole solution was stirred for 60 minutes. The resulting solution was concentrated under reduced pressure. To the residue was added cold water and the precipitated solid was filtered off. The precipitate was dissolved into ethanol under heating, and active carbon was added to the solution. The mixture was filtered to give 25.9 g of the title compound, m.p. 188.5°–198.5° C.

EXAMPLE 3

2-(4-n-Hexadecyloxyphenyl)-5-(4-chlorophenoxy)-4-oxazoleacetic acid

To a solution of 19 g of 4-(n-hexadecyloxy)benzoyl chloride and 11.9 g of β-ethyl L-aspartate hydrochloride in 200 ml of tetrahydrofuran with stirring under ice-cooling was dropwise added 55 ml of triethylamine. With further stirring for 130 minutes, the reaction mixture was poured into diluted hydrochloric acid and the mixture was extracted with ethyl acetate. The organic layer was washed with water, dried anhydrous sodium sulfate and concentrated under reduced pressure. A part of residual β-ethyl N-(4-n-hexadecyloxybenzoyl)-L-aspartate (a white solid, 18.1 g) which is not purified was dissolved into 200 ml of ethyl acetate. To the resulting solution were added 9.2 g of p-chlorophenol and 7.4 g of dichlorohexylcarbodiimide and the mixture was stirred at room temperature for 60 minutes. The precipitated dicyclohexylurea was filtered off. The filtrate was concentrated and the residue was vacuum distilled.

After removing the forerun (excess p-chlorophenol) only, the residue was dissolved in 100 ml of toluene. With addition of 15 ml of phosphorus oxychloride, the solution was refluxed under heating for 210 minutes. After cooling, the mixture was poured into a mixture of ice and potassium carbonate for decomposition and the mixture was extracted with ethyl acetate. The organic layer was washed with water, dried over anhydrous sodium sulfate and concentrated under reduced pressure. The residue obtained was dissolved in 100 ml of acetone. To the solution was added an aqueous solution of 3.0 g of sodium hydroxide and the solution was stirred at room temperature for 30 minutes. The resulting mixture was concentrated under reduced pressure. After addition of ice-water, the residue was acidified with hydrochloric acid. The separated solid was filtered off, dried and recrystallized from methanol. The crystals thus obtained were filtered off and further recrystallized from hexane to give 6 g of the title compound as a white fine powder, m.p. 76°–77° C.

The following compounds can be prepared in the same manner as in the above example.

2-[4-n-(9-Octadecenyl)oxyphenyl]-5-ethoxy-4-oxazoleacetic acid, m.p. 75.5°–76.5° C.

2-[4-(4-Chlorobenzylamino)phenyl]-5-ethoxy-4-oxazoleacetic acid

2-[4-(4-Chlorobenzylthio)phenyl]-5-phenoxy-4-oxazoleacetic acid

While the invention has been explained in detail with references to the above description and examples included therein, various alterations and modifications can apparently be made without departing from the spirit and scope of the invention.

We claim:

1. Ethyl 2-(4-n-hexadecyloxyphenyl)-5-ethoxyoxazoleacetate.

2. 2-(4-n-Hexadecyloxyphenyl)-5-ethoxy-4-oxazoleacetic acid.

3. Sodium 2-(4-n-hexadecylaminophenyl)-5-ethoxy-4-oxazoleacetate.

* * * * *